United States Patent
Martens et al.

(10) Patent No.: US 9,387,318 B2
(45) Date of Patent: Jul. 12, 2016

(54) TISSUE STIMULATION METHOD AND APPARATUS

(75) Inventors: Hubert Cecile Francois Martens, Eindhoven (NL); Michel Marcel Jose Decre, Eindhoven (NL); Eugenio Cantatore, Eindhoven (NL)

(73) Assignee: Medtronic Bakken Research Center B.V, Maastricht (NL)

( * ) Notice: Subject to any disclaimer, the term of this patent is extended or adjusted under 35 U.S.C. 154(b) by 662 days.

(21) Appl. No.: 12/442,862

(22) PCT Filed: Sep. 21, 2007

(86) PCT No.: PCT/IB2007/053844
§ 371 (c)(1),
(2), (4) Date: Mar. 25, 2009

(87) PCT Pub. No.: WO2008/038208
PCT Pub. Date: Apr. 3, 2008

(65) Prior Publication Data
US 2010/0030298 A1    Feb. 4, 2010

Related U.S. Application Data

(60) Provisional application No. 60/826,918, filed on Sep. 26, 2006.

(51) Int. Cl.
*A61N 1/05* (2006.01)
*A61N 1/04* (2006.01)

(52) U.S. Cl.
CPC ............ *A61N 1/0529* (2013.01); *A61N 1/0472* (2013.01); *A61N 1/0476* (2013.01); *A61N 1/05* (2013.01)

(58) Field of Classification Search
CPC . A61N 1/0529; A61N 1/0472; A61N 1/0476; A61N 1/05
USPC .............................. 607/115–118, 45, 139, 152
See application file for complete search history.

(56) References Cited

U.S. PATENT DOCUMENTS 4,819,647 A    4/1989    Byers
5,843,148 A    12/1998    Gijsbers et al.
(Continued)

FOREIGN PATENT DOCUMENTS

EP    1602393 A    12/2005
EP    1602393 A1    12/2005
(Continued)

OTHER PUBLICATIONS

Lovell, N.H. et al "Simulation of Parallel Current Injection for use in a Vision Prosthesis" Proc. of the 2nd Int'l IEEE EMBS Conf. on Neural Engineering, Mar. 2005, pp. 458-461.
(Continued)

*Primary Examiner* — Edward Moran
*Assistant Examiner* — Michael Carey
(74) *Attorney, Agent, or Firm* — Shumaker & Sieffert, P.A.

(57) ABSTRACT

A stimulation apparatus includes a stimulation lead (102), a multiplexer (114), a stimulation signal generator (116), and a signal detector (120). The stimulation lead (102) includes a plurality of stimulation electrodes (112) disposed in an array about a distal portion of the lead body (110). The arrangement of the electrodes (112) facilitates the controlled steering of stimulating electrical field (118) in three dimensions. Four dimensional field steering may also be provided.

42 Claims, 10 Drawing Sheets

(56) References Cited

U.S. PATENT DOCUMENTS

| | | |
|---|---|---|
| 5,895,416 A | 4/1999 | Barreras |
| 6,038,480 A | 3/2000 | Hrdlicka |
| 6,762,510 B2 | 7/2004 | Fock |
| 7,308,317 B1 * | 12/2007 | Okandan ............... A61N 1/0543 607/115 |
| 7,917,231 B2 * | 3/2011 | Farah et al. ................... 607/116 |
| 2004/0186544 A1 | 9/2004 | King |
| 2005/0070982 A1 | 3/2005 | Heruth |
| 2005/0171587 A1 | 8/2005 | Daglow et al. |
| 2007/0027515 A1 * | 2/2007 | Gerber ..................... A61N 1/05 607/116 |
| 2007/0060815 A1 * | 3/2007 | Martin et al. ................. 600/372 |
| 2012/0158114 A1 * | 6/2012 | Debruyne et al. ............. 607/137 |

FOREIGN PATENT DOCUMENTS

| | | |
|---|---|---|
| EP | 1723983 A | 11/2006 |
| EP | 1723983 A1 | 11/2006 |
| JP | 2000-508201 | 7/2000 |
| JP | 2003-522004 | 7/2003 |
| JP | 2005-515819 | 6/2005 |
| RU | 2029572 C1 | 2/1995 |
| RU | 2145242 C1 | 2/2000 |
| RU | 2146155 C1 | 3/2000 |
| RU | 2181300 C1 | 4/2002 |
| WO | 94/15528 A1 | 7/1994 |
| WO | 02/45795 A1 | 6/2002 |
| WO | 200245795 A2 | 6/2002 |
| WO | WO 03/028521 A2 * | 10/2003 |
| WO | 2004/000416 A1 | 12/2003 |

OTHER PUBLICATIONS

English translation of an Office Action dated Sep. 21, 2011 for Russian Patent Application No. 2009115722.

European Search Report dated Dec. 10, 2012 for European Patent Application No. 12 19 2194.

Notice of Reasons for Rejection mailed on Jun. 26, 2012 for Japanese Patent Application No. 2009-529817.

Office Action for European Patent Application No. 07 826 496.7 dated Jan. 23, 2012.

Decision on Grant of a Patent for Invention for Russian Patent Application No. 2009115722/14.

Notice of Reasons for Rejection for Japanese Patent Application No. 2009-529817 mailed on Jan. 22, 2013.

Office Action dated Feb. 6, 2014 for European Patent Application No. 12192194.4.

Notification to Grant Patent Right for Invention dated May 24, 2013 for Chinese Patent Application No. 200780035680.9.

* cited by examiner

TISSUE STIMULATION METHOD AND APPARATUS

The present application relates to neural stimulation therapy, and especially to deep brain stimulation. It also finds application to the electrical stimulation of muscle and other tissue.

Conventional techniques for treating neurological diseases and other disorders have included the use of drugs and resective surgery (i.e., the surgical removal of diseased brain/nerve tissue). Unfortunately, however, these treatments have various disadvantages. For example, drug therapy may produce significant side effects, and not all patients respond to the treatment (e.g., about thirty percent (30%) of epilepsy patients are drug resistant). Resective surgery can carry a relatively high risk. Moreover, resective surgery is not reversible, and not all patients are eligible.

An alternative treatment for neurological disorders is neurostimulation therapy, in which an external or implanted device is used to apply electric or magnetic stimuli to the neural tissue. Neurostimulation can be used to treat a number of different diseases, including Parkinson's disease, epilepsy, chronic pain, depression, Alzheimer's disease, obsessive compulsive disorders, and even obesity. Where drug therapy has failed and/or surgery is not possible, neurostimulation therapy can also be a treatment of last resort. For example, researchers have estimated that at least fifteen percent (15%) of all epilepsy patients can only be helped with neurostimulation.

To achieve the therapeutic benefit, however, the stimulus must be delivered at the appropriate target location in the tissue. In case of electrical stimulation of tissues, one often places a lead with electrodes near the target. By delivering a current through the electrode(s) an electrical field is created within the body. In practical systems this has been achieved by carefully positioning the leads near the target. In more sophisticated systems, field steering has been used to adjust the position of the electric field. More particularly, currents are applied through multiple electrodes located in the vicinity of the stimulation target. The resulting electrical field can be steered by adjusting the current balances. See U.S. Pat. No. 5,843,148 to Gijsbers et al., *High Resolution Brain Stimulation Lead and Method of Use*; U.S. Pat. No. 5,895,416 to Barreras, et al., *Method and Apparatus for Controlling and Steering an Electric Field*; U.S. Pat. No. 6,038,480 to Hrdlicka, et al., *Living Tissue Stimulation and Recording Techniques with Local Control of Active Sites*; U.S. Patent Publication No. 2004/0186544A1 to King, *Electrical Tissue Stimulation Apparatus and Method*; U.S. Patent Publication No. 2005/0070982 to Heruth, *Field Steerable Electrical Stimulation Paddle, Lead System, and Medical Device Incorporating The Same*; Lovell, et al., *Simulation of Parallel Current Injection for Use in a Vision Prosthesis*, Proceedings of the $2^{nd}$ International IEEE EMBS Conference on Neural Engineering, Arlington, Va., Mar. 16-19, 2005, pg. 458-461.

Nonetheless, there remains room for improvement. For example, it is desirable to provide still additional flexibility in positioning the lead and adjusting the stimulating electrical field.

Aspects of the present application address these matters and others.

In accordance with one aspect, a tissue stimulation apparatus includes a stimulation lead having a longitudinal axis and a plurality of electrodes carried by the lead and disposed about the longitudinal axis in a two-dimensional array. The lead is insertable in a tissue to be stimulated in a direction substantially parallel to the longitudinal axis. A stimulating field generated by an electrode is steerable in at least three dimensions.

According to another aspect, a tissue stimulation method includes the steps of inserting a stimulation lead in a tissue of interest, exciting a first stimulating electrode so as to generate a stimulating electric field, and varying an electrical stimulus applied to at least first and second shielding electrodes so as to vary a distribution of the stimulating electric field in three spatial dimensions. The lead includes a plurality of electrodes disposed angularly about a longitudinal axis.

According to another aspect, a tissue stimulation apparatus includes a stimulation lead having a longitudinal axis. The lead includes a substantially rotationally symmetric exterior cross section. The lead also includes a plurality of stimulation electrodes carried by the lead and disposed about the longitudinal axis in a two-dimensional close-packed array.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 6A:
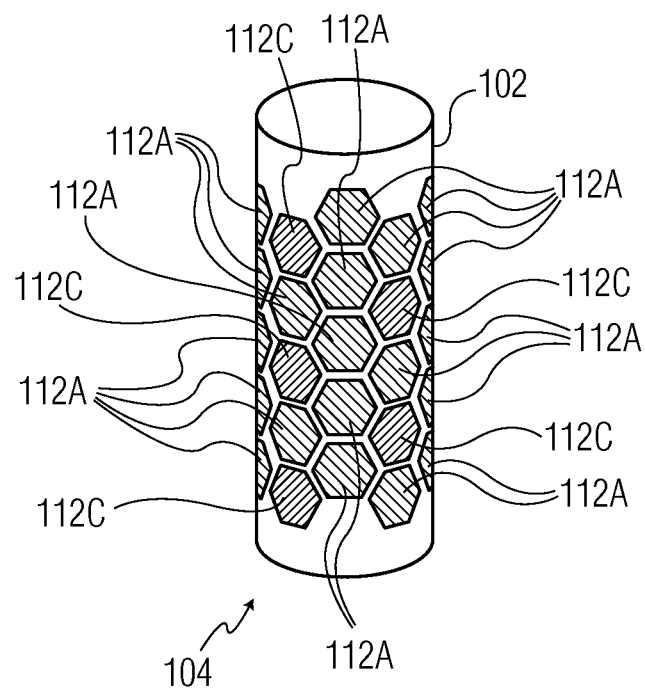
Figure 6B:
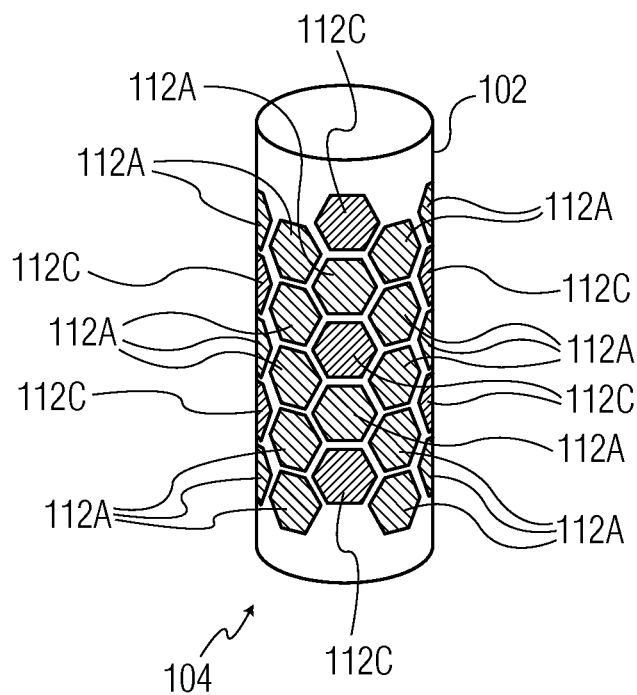
Figure 6C:
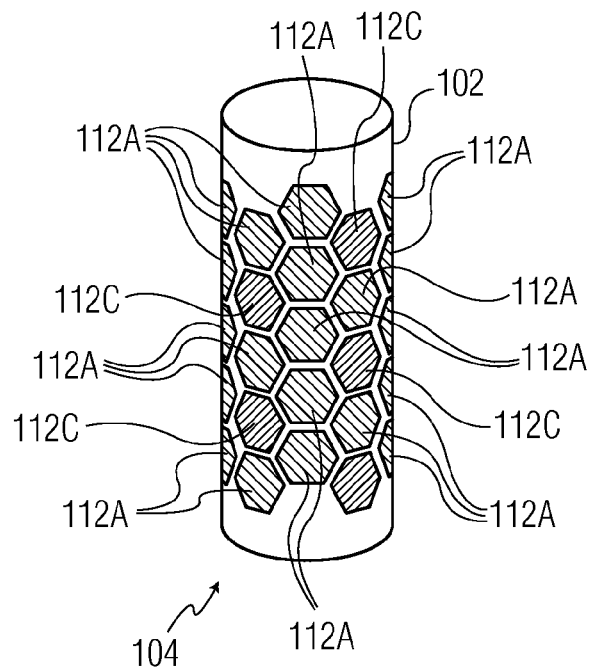

FIGS. 6A, 6B, and 6C depict a time-varying electrical stimulation scheme.

Figure 7A:
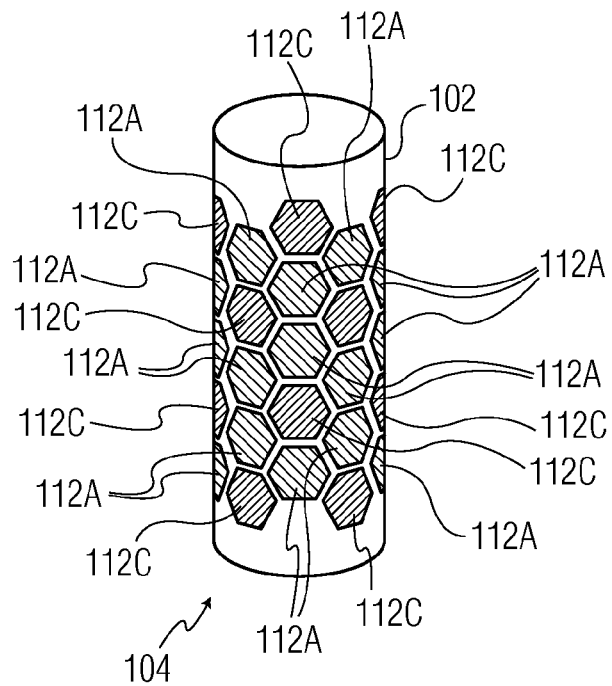
Figure 7B:
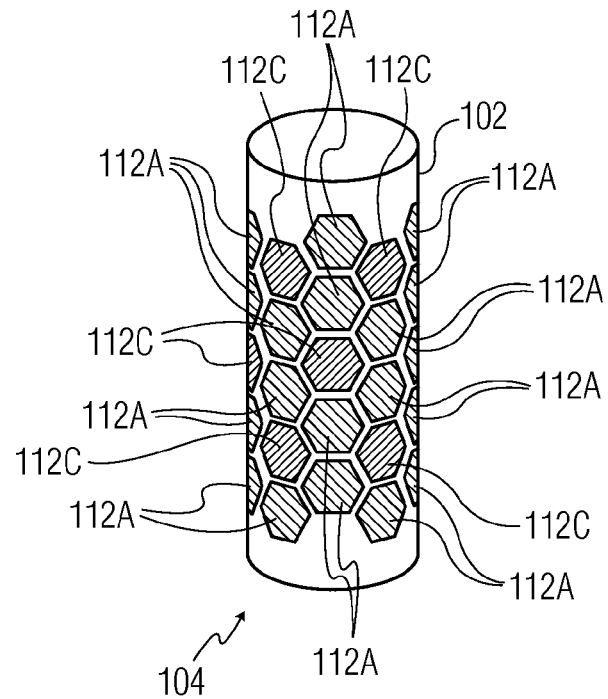
Figure 7C:
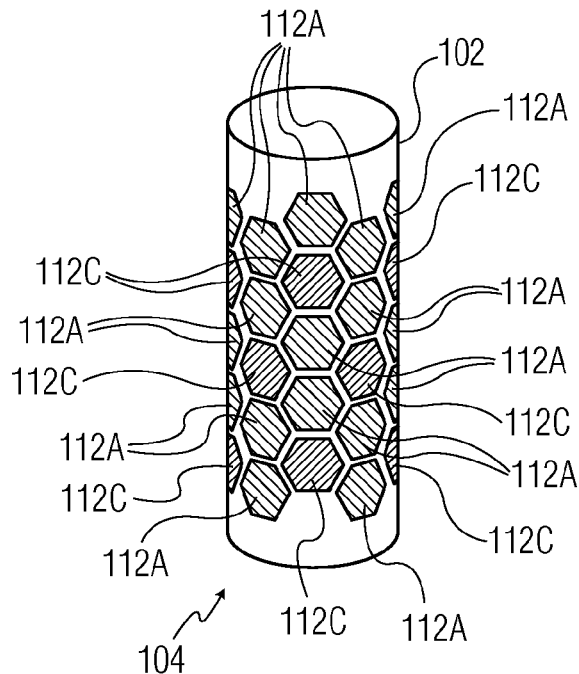

FIGS. 7A, 7B, and 7C depict a time-varying electrical stimulation scheme.

Figure 8A:
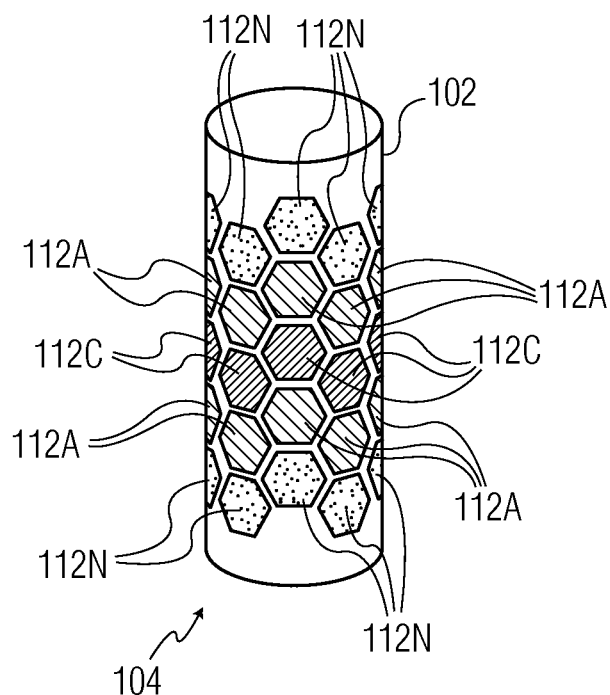
Figure 8B:
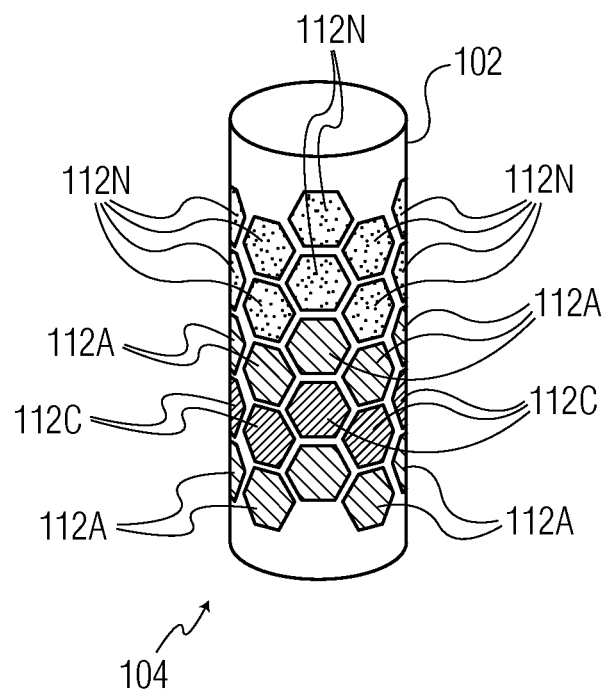

FIGS. 8A and 8B depict a time-varying electrical stimulation scheme.

Figure 9A:
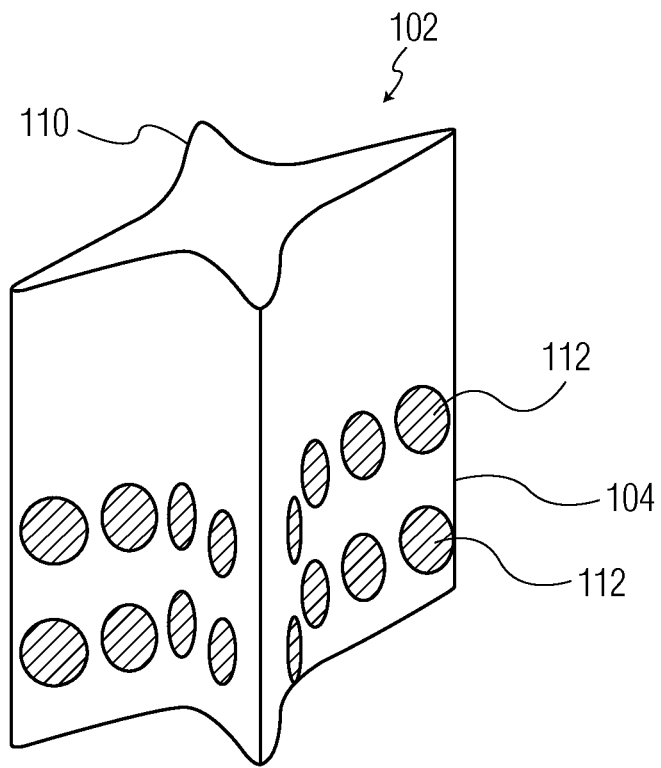
Figure 9B:
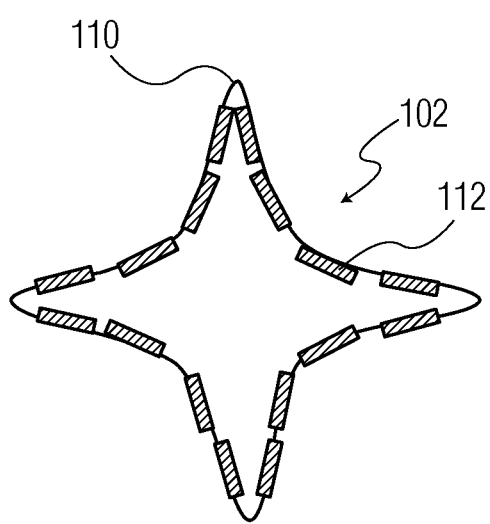

FIGS. 9A and 9B are perspective and cross-sectional views of a stimulation lead, respectively.

Figure 10:
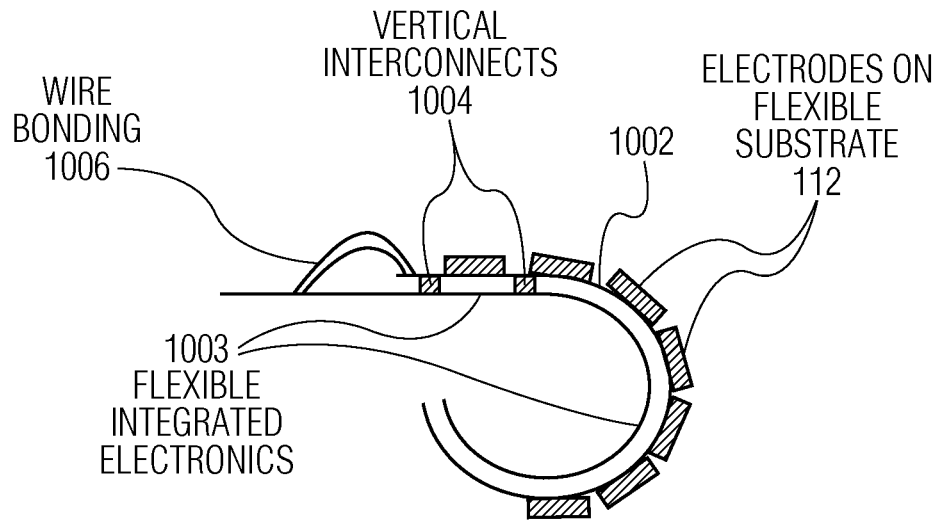

FIG. 10 is a cross-sectional view depicting a construction of a stimulation lead.

Figure 1:
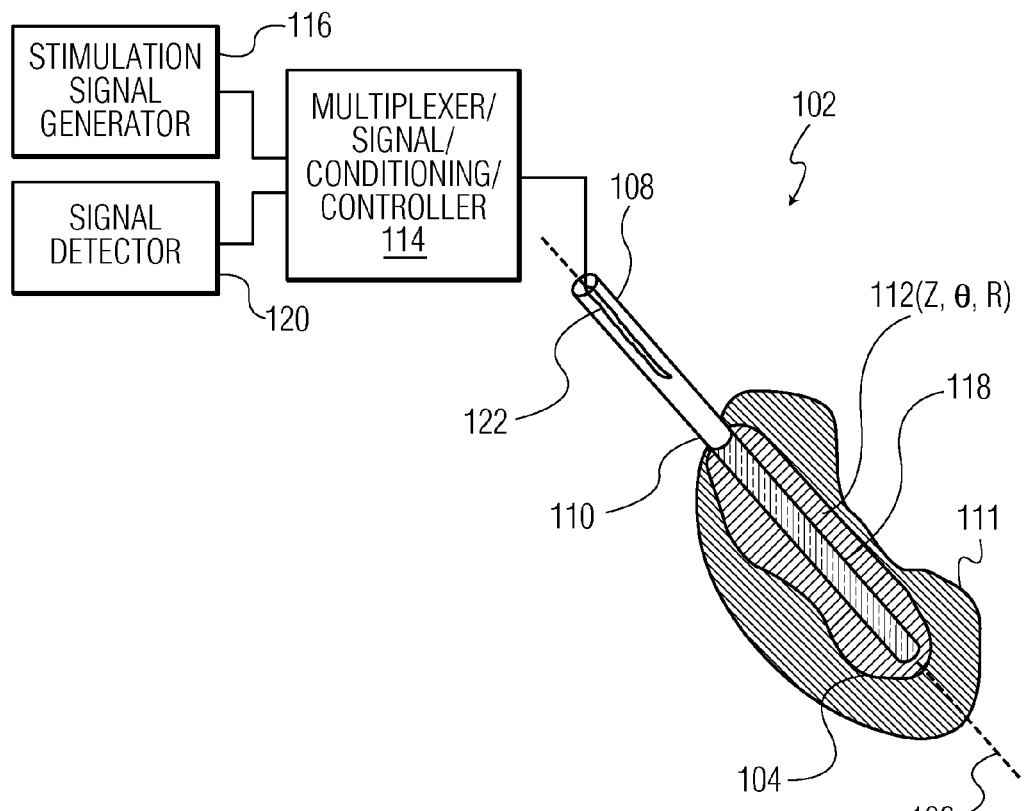
FIG. 1 depicts a stimulation apparatus.
Figure 11:
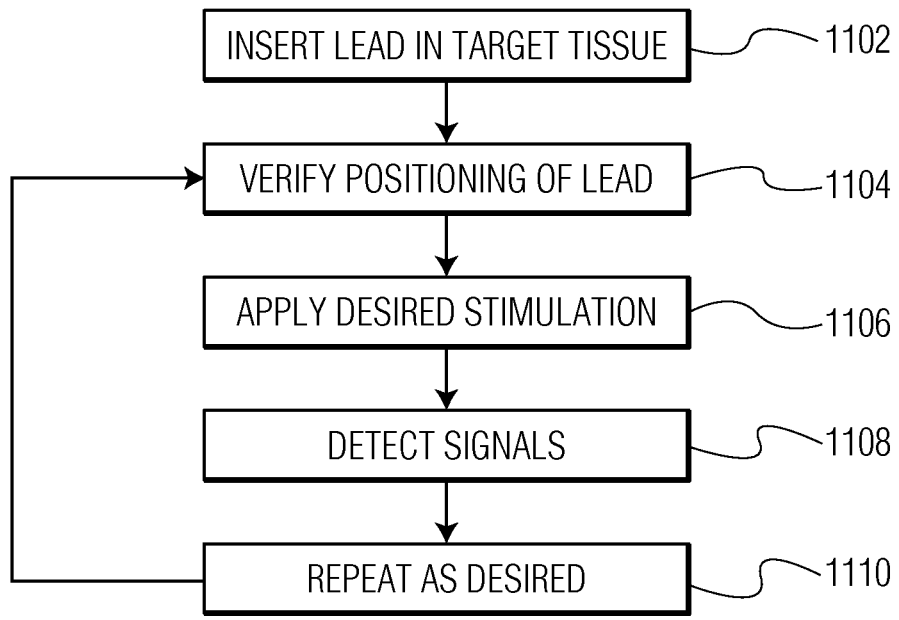

FIG. 11 depicts a stimulation method. With reference to FIG. 1, an implantable tissue stimulation lead 102 includes a distal end 104, a longitudinal axis 106, a proximal end 108, and a body 110. As illustrated in FIG. 1, the body 110 has a generally cylindrical exterior shape.

To facilitate positioning of the lead 102 about its longitudinal or z-axis 106, at least a portion of the lead 102 carries a fiducial marker or markers 122 which serve to identify a rotational orientation of the lead 102. As illustrated in FIG. 1, a proximal portion of the body 110 includes a flat, groove, protrusion, marking or other rotationally asymmetric identifier which facilitates the visual or tactile identification of the rotational orientation of the lead 102.

The distal end 104 of the lead 102 is implanted within or otherwise in the vicinity of the tissue of interest or target region 111, for example in the brain, spinal column, or muscle tissue. The lead 102 also carries an array of electrodes 112 disposed about the distal portion of the body 110. The electrodes 112 may include stimulation electrodes, signal detection electrodes, dual purpose electrodes, or a desired combination thereof.

Figure 2:
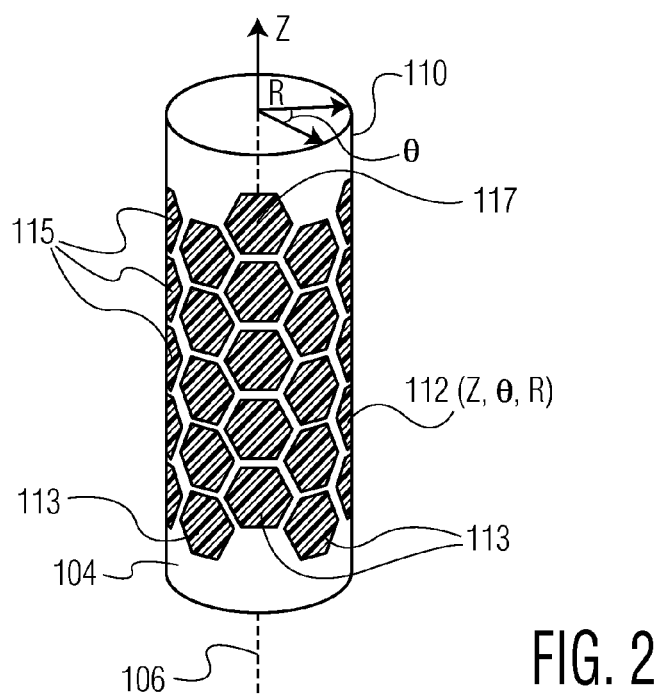
FIG. 2 depicts a portion of a stimulation lead.

With additional reference to FIG. 2, the electrodes 112 are arranged in a two-dimensional (2D) close-packed array having a plurality of angularly spaced columns 113 and longitudinally spaced rows 115. Adjacent columns 113 are offset in the z-direction by one-half the electrode 112 longitudinal array spacing. Adjacent rows 115 are likewise angularly offset by one-half the electrode 112 angular array spacing.

The angular position of each electrode 112 can be expressed in terms of a cylindrical coordinate system which includes a longitudinal position Z, an angular position θ, and a radial position R with respect to the longitudinal axis 106. In this regard, it should be noted that the electrodes 112 and the fiducial marker(s) 122 have a known angular relationship. In the exemplary case of a cylindrical lead, the electrodes 112 have a common radial position R.

As illustrated, the electrodes 112 have a generally hexagonal shape and thus exhibit six-fold symmetry about their respective centroids 117. As will be described in greater detail below, the electrodes 112 can be driven according to a variety of electrical stimulation schemes so as to provide a controlled steering of a stimulating electrical field 118 both temporally and in three spatial dimensions.

Electrical and mechanical connections between the lead 102 and the external environment are provided through the proximal end 108. The stimulation signal generator 116 supplies electrical energy to the electrodes 112 so as to generate a desired stimulation electrical field 118 in the target region 111. The signal detector 120 includes requisite amplification, signal conditioning and other functionality for receiving signals from the electrodes 112. In one implementation, some or all of the electrical circuitry used to produce the stimulation and/or sense signals is integrated into the lead 102. In another implementation, the electrical circuitry is contained in the signal generator 116 and/or the signal detector 120, or in an intermediate location. In this regard, it should be noted that locating amplification and other signal conditioning circuitry relatively closer to the electrodes 112 tends to reduce the effects of electrical noise.

An optional signal multiplexer 114 multiplexes electrical signals between the electrodes 112, a stimulation signal generator 116 and/or a signal detector 120. The signal multiplexer 114 and other desired signal conditioning, controllers, and like circuitry may be carried by the lead 102, mounted externally to the lead 102 in proximity thereto, or mounted in proximity to the stimulation signal generator 116 or detector 120.

Figure 3:
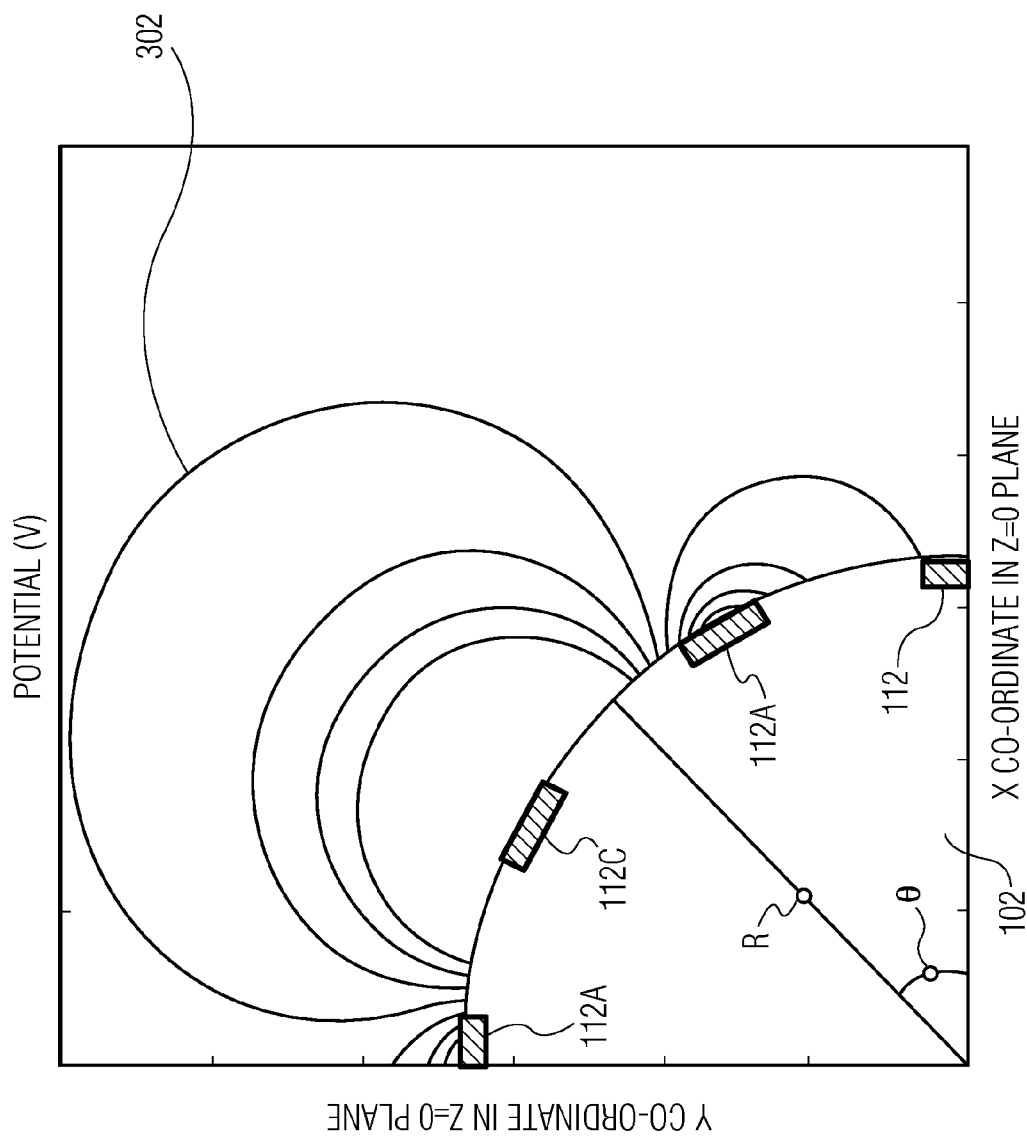
FIG. 3 depicts a field distribution generated by a stimulation apparatus.

FIG. 3 is a simulation result showing a stimulating electrical field 302 generated in the case of a lead 102 having rows containing twelve (12) electrodes 112 equally spaced along the circumference (i.e., with a thirty degree (30°) centre-to-centre angle between electrodes). Subsequent rows are shifted by fifteen degrees (15°) along the circumference, resulting in a hexagonal pattern around the lead 102. A central electrode $112_C$ is put to cathodal stimulation and six (6) surrounding electrodes $112_A$ are put to anodal stimulation at ⅙ of the cathodal amplitude (so the sum of cathodal and anodal amplitudes equals 0).

Thus, the cathodal electrode $112_C$ can be considered as a stimulation electrode and the anodal electrodes $112_A$ as shielding electrodes. More particularly, the field generated by the anodal electrodes $112_A$ serves to limit the stimulating field generated by the cathodal electrode $112_C$ to a smaller region than would otherwise be the case.

Though FIG. 3 depicts the field distribution 302 in an azimuthal plane, those of ordinary skill in the art will appreciate that the stimulating field also extends in the z-direction.

The spatial distribution of the stimulating field can be varied by varying the relative electrical stimuli applied to the various electrodes 112. For example, the relative electrical stimuli applied to the anodic electrodes $112_A$ can be varied to provide other lower-order symmetric or asymmetric field distributions 302. Viewed from the perspective of the lead 102, varying the relative electrical stimuli varies the spatial distribution of the field in both the angular and longitudinal directions. Varying the magnitude of the electrical stimuli applied to the various electrodes 112 likewise varies the distribution in the radial dimension. Thus, the field shaping properties of the electrodes 112 can be used to provide a controlled, steering of the stimulating electrical field 118 in three spatial dimensions.

Figure 4A:
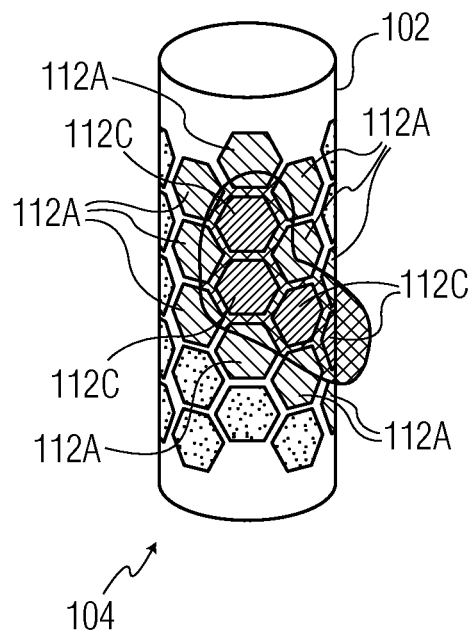
FIGS. 4A and 4B depict electrical stimulation schemes.

An example of a bipolar electrical stimulation scheme involving multiple cathodal or stimulating electrodes $112_C$ is shown schematically in FIG. 4A. As illustrated, the cathodal electrodes $112_C$ cooperate with anodal or shielding electrodes $112_A$ to generate a stimulating electrical field 402 of substantially arbitrary shape.

Figure 4B:
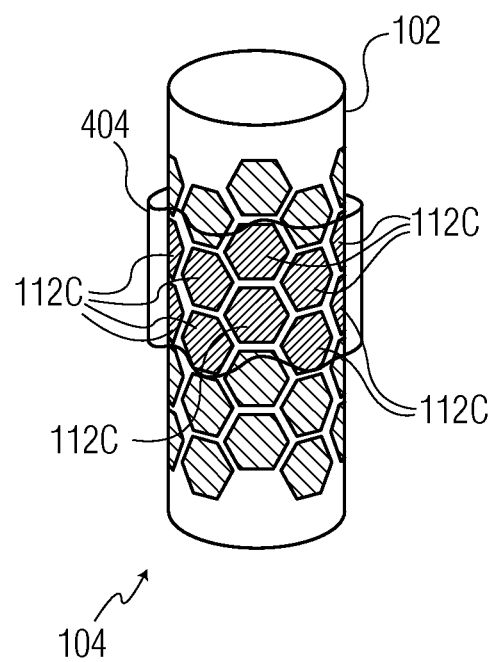

An example of a unipolar electrical stimulation scheme involving multiple cathodal or stimulating electrodes $112_C$ is shown schematically in FIG. 4B. As illustrated, the cathodal electrodes $112_C$ generate a stimulating electrical field 404 which exhibits rotational symmetry about the lead's longitudinal axis 106.

Various unipolar or bipolar time varying electrical stimulation schemes may also be used to provide field steering in a temporal dimension.

Figure 5A:
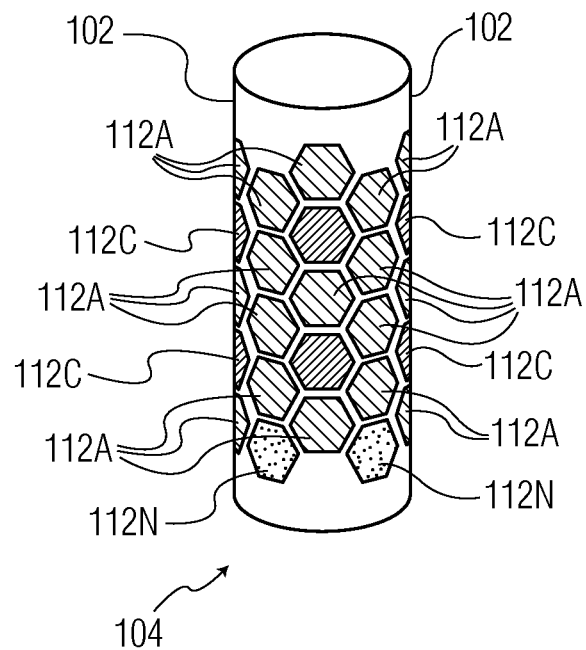
FIGS. 5A and 5B depict a time-varying electrical stimulation scheme.
Figure 5B:
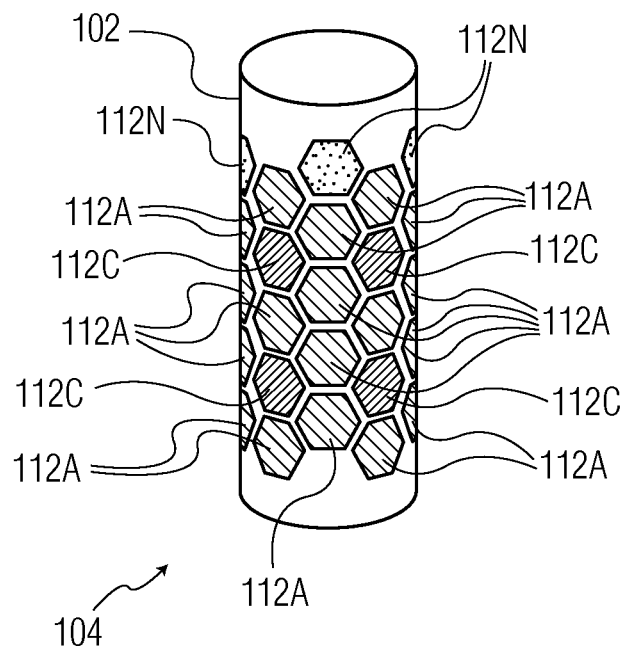

FIG. 5 depicts a first example of a time-varying electrical stimulation scheme, where FIG. 5A depicts the electrical stimulus applied to the various electrodes 112 at time $t_0$ and FIG. 5B depicts the electrical stimulus applied to the various electrodes at time $t_1$. As will be appreciated, the electrical stimulation sequence may be repeated as desired so that the stimulation field alternates between first and second positions with respect to the probe longitudinal axis 106. Combinations of electrode schemes and time steps that can generate a rotating excitation field can also be readily devised. Note that, in the illustrated example, certain of the electrodes $112_N$ are substantially unexcited and thus do not substantially stimulate or shield the applied stimulation field. Note also that the stimulation pattern exhibits rotational symmetry.

Another example of a time-varying electrical stimulation scheme is shown in FIG. 6, where FIG. 6A shows the electrical stimuli applied at time $t_0$, FIG. 6B shows the electrical stimuli applied at time $t_1$, FIG. 6C shows the electrical stimuli applied at time $t_2$, and so on. Note that the resultant stimulation field again exhibits rotational symmetry.

Another time-varying bipolar electrical stimulation scheme is shown in FIG. 7, where FIG. 7A shows the electrical stimuli applied at time $t_0$, FIG. 7B shows the electrical stimuli applied at time $t_1$, and FIG. 7C shows the electrical stimuli applied at time $t_2$. Note that the stimulating electric field is both rotationally and longitudinally asymmetric.

Still another time-varying bipolar electrical stimulation scheme is shown in FIGS. 8A and 8B at times $t_0$ and $t_1$ respectively. Note that the resultant stimulating electric field exhibits rotational but not longitudinal symmetry. The sequence may also be repeated so as to provide a stimulating field at still additional longitudinal positions.

The foregoing are but a few of examples of possible static and temporally-varying electrical stimulation schemes and the resultant stimulating fields, as other bipolar and/or unipolar electrical stimulation schemes may be used to generate stimulating electric fields of substantially arbitrary spatial and/or temporal extent. In this regard, it should be noted that time-varying stimulating fields may also be generated by varying the magnitude and/or relative electrical stimuli applied to one or more cathodal $112_C$ or anodal $112_A$ electrodes. In FIG. 3, for example, the electrical stimulus applied to one or more of the anodal electrodes $112_A$ may be varied so that the stimulating field includes a lobe or protrusion which rotates about the centroid 117 of the cathodal electrode $112_C$. As another example, the magnitude of the electrical stimulation may be varied so as to vary the spatial extent of the stimulating field as a function of time. Of course, both the absolute and relative electrical stimulation may be varied together in a coordinated or otherwise desired fashion.

As yet another example, the time-varying electrical stimuli may be applied at a relatively high rate so as to modulate the extent of the stimulating field and thus approximate a stimulating field which is not otherwise achievable with a given electrode 112 configuration. This is for instance achieved by the time-averaged effect of the time-varying excitation pattern on the excited tissue. A particular advantage of such a modulation technique is that relatively higher spatial resolutions may be provided. Viewed from another perspective, a desired spatial resolution may be obtained with a relatively simplified lead 102.

Note that while the polarities of the various electrodes 112 have been described in the context of cathodal stimulation, field distributions of equivalent but opposite polarity may be obtained by reversing the polarity of the applied electrical stimuli.

Still other lead 102 and electrode 112 configurations are contemplated. For example, the body 110 may take various non-circular cross sections, either with or without rotational symmetry. The electrodes 112 may also take circular, square, irregular, or other non-hexagonal shapes. In one implementation, the electrodes 112 exhibit n-fold symmetry about their respective centroids 117, where n is an integer greater than or equal to three (3). The various rows 115 and columns 113 of the electrode 112 array need not be offset. The electrodes 112 may also be arranged in an irregular array, for example where one (1) or more of the electrodes 112 have different shapes, sizes, or spacings. As yet another example, one or more configurations of multiple electrodes 112 may be repeated.

An example of a lead 102 having a non-circular cross section is shown in FIGS. 9A and 9B. As illustrated, the body 110 takes a generally star or cross-shaped exterior cross section. Also as illustrated, the electrodes 112 have a circular shape; the rows and columns of the array are not offset.

The fiducial markers 122 may also take various forms. For example, a distal portion 104 of the lead may also exhibit rotational asymmetry. As the distal portion 104 is typically inserted in the tissue 111 of the patient and thus may not be visible during use, the fiducial marker(s) 122 are preferably configured so as to be visible in a desired imaging modality or modalities such as x-ray, computed tomography, magnetic resonance, or nuclear imaging. Thus, the distal portion 104 may include one or more flats, grooves, material free regions, or the like. The lead 102 may also include one more regions which contain a material which is relatively more (or less) contrasty in the desired modality or modalities.

The fiducial marker(s) 122 may also be used to facilitate the positioning of the lead in a stereotactic head frame or other external holding device. According to such an arrangement, the proximal portion 108 of the lead 102 includes a slot, groove, keyway, or the like which engages a corresponding structure on the external holding device. To provide positioning flexibility, one or both of the lead 102 and the holding device may be configured to allow the user to selectively adjust the position of the lead 102 as desired. Alternatively to mechanical positioning methods, various sensing methods can also be used to provide fiducial markers, such as optical, magnetic, electrical, chemical, and the like.

An exemplary lead construction which provides an improved integration of the electrodes 112 and an electrical circuit is depicted FIG. 10. The electrodes 112, which are fabricated from platinum, platinum/iridium, platinum black, or other known, biocompatible materials, are carried by a flexible circuit substrate 1002. The substrate, which is fabricated from a polyimide, polycarbonate, polyester, or other suitable material, also carries circuit traces which provide the requisite electrical connections to the electrodes 112.

Where the lead 102 contains signal conditioning, multiplexing, control, or other integrated electronics, a flexible monolithic electrical circuit 1003 may also be provided. Details of such a circuit are discussed more fully in U.S. Pat. No. 6,762,510 B2 to Fock, et al., entitled Flexible Integrated Monolithic Circuit, which patent is expressly incorporated by reference in its entirety herein. Interconnections between the various layers are provided through vertical interconnects 1004 and/or wire bonds 1006. The electrodes 112 and electrical circuitry 1003 may also be combined on a unitary substrate.

A particular advantage of such a configuration is its mechanical flexibility, which allows the assembly to follow a curved surface. Note also that the electronics may also be implemented using conventional rigid chips which are suitably electrically connected to the substrate 1002, for example through vertical interconnects and/or wire bonds. Such a configuration is particularly well suited to situations in which the chips are small enough to allow the substrate 1002 to form a lead having a desired radius or other curvature.

Operation of the apparatus will now be described in relation to FIG. 11.

The lead 102 is inserted in the target tissue at step 1102. To take full advantage of the three dimensional spatial field steering capabilities of the lead 102, the lead 102 is advantageously positioned in the tissue so that the tissue to be stimulated surrounds at least a longitudinal portion of the lead. The tactilely, visually or otherwise identifiable fiducial marker 122, if any, may be used as a rotational positioning aid. Positioning may also be aided through the use of a stereotactic frame or other positioning device, whereupon the lead is locked or otherwise secured in position.

The positioning of the lead 102 is optionally verified or registered at step 1104. Where the lead 102 contains fiducial marker(s) 122 which are visible in an imaging modality, the positioning may be verified using a suitable imaging examination. The position may also be verified by exciting one or more of the electrodes 112 and observing the response using a functional imaging modality such as functional magnetic resonance imaging (fMRI) or positron emission tomography (PET). Where the lead 102 contains one or more dedicated or multiplexed sensing electrodes, biological signals sensed by the electrodes may be also used to understand or otherwise verify the position of the lead 102. As will be appreciated, determining the longitudinal and rotational positions of the lead 102 fixes the absolute location of each electrode 112 in relation to the anatomy of the patient. This information can be used to select the optimum stimulation patterns.

The desired electrical stimulation is applied at step 1106 so as to generate the desired stimulating field. As noted above, the stimulation may be substantially static or time invariant; time-varying electrical stimuli may also be applied.

Where the lead 102 contains one or more dedicated or multiplexed sensing electrodes, biological signals may also be detected and/or monitored at step 1108.

At step 1110, one or more of the positioning 1104, stimulation 1106, and detection 1108 steps are repeated as desired. Note that the various steps may be performed in a desired order; some or all may also be performed concurrently.

Having thus described the preferred embodiments, what is claimed is:

1. An apparatus comprising:
   a lead having a longitudinal axis, the lead configured to be inserted in a tissue in a direction substantially parallel to the longitudinal axis; and
   a plurality of electrodes carried on a portion of the lead and disposed about the longitudinal axis in a two-dimensional array on the portion of the lead, each electrode having an n-fold rotational symmetry, n being an integer greater than or equal to three, wherein the portion of the lead on which the plurality of electrodes are carried has a substantially constant width along the longitudinal axis, and
   wherein a field generated by delivery of electrical stimulation via the electrodes is steerable in three dimensions.

2. The apparatus of claim 1, wherein the two-dimensional array includes a close-packed array.

3. The apparatus of claim 1, wherein n is an integer greater than or equal to six.

4. The apparatus of claim 1, wherein the two-dimensional array includes an irregular array.

5. The apparatus of claim 1 further comprising
   a fiducial marker carried by the lead, wherein the fiducial marker identifies a rotational orientation of the lead.

6. The apparatus of claim 5, wherein the fiducial marker is configured to be visible during imaging when the lead is implanted in the tissue.

7. The apparatus of claim 1, wherein the lead includes a substantially circular exterior cross-section and the tissue is neural tissue.

8. A method comprising:
   applying an electrical stimulus to a first stimulating electrode of a plurality of electrodes of a lead implanted in tissue to generate an electric field, wherein the plurality of electrodes are carried on a portion of the lead and disposed angularly about a longitudinal axis of the lead, each electrode having an n-fold rotational symmetry, n being an integer greater than or equal to three, wherein the portion of the lead on which the plurality of electrodes are carried has a substantially constant width along the longitudinal axis; and
   varying the electrical stimulus applied to at least first and second shielding electrodes to vary a distribution of the electric field in three spatial dimensions.

9. The method of claim 8, wherein the lead carries a fiducial marker which identifies a rotational orientation of the lead and wherein the method further comprises applying the electrical stimulus based on a location of the fiducial marker.

10. The method of claim 8, wherein a proximal portion of the lead carries a fiducial marker which provides at least one of a tactile or visual indication of a rotational orientation of the lead and wherein the method further comprises using the fiducial marker to determine a position of the lead in relation to the tissue.

11. The method of claim 8 further comprising using at least one of the plurality of electrodes to sense a biological signal.

12. The method of claim 8, wherein the tissue is brain tissue.

13. An apparatus comprising:
    a lead having a longitudinal axis, wherein the lead includes a substantially rotationally symmetric exterior cross section; and
    a plurality of electrodes carried on a portion of the lead and disposed about the longitudinal axis in a two-dimensional close-packed array on the portion of the lead, each electrode having an n-fold rotational symmetry, n being an integer greater than or equal to three, wherein the portion of the lead on which the plurality of electrodes are carried has a substantially constant width along the longitudinal axis.

14. The apparatus of claim 13 further comprising fiducial marking means for indicating a rotational orientation of the lead.

15. The apparatus of claim 13 further comprising means for determining a location of one of the plurality of electrodes within tissue and selectively applying an electrical stimulus to the electrode based on the determined location.

16. The apparatus of claim 1, wherein the electrodes are each hexagonal in shape.

17. The apparatus of claim 1, further comprising a stimulation generator configured to generate the electrical stimulation delivered via the electrodes and a controller configured to control the steering of the field generated by the delivery of the electrical stimulation.

18. The apparatus of claim 17, further comprising an implantable medical device configured to be coupled to the lead, wherein the implantable medical device includes at least one of the stimulation generator or the controller.

19. The apparatus of claim 17, wherein the controller is configured to control the steering of the field by at least applying an electrical stimulus via a first stimulating electrode of the plurality of electrodes to generate an electric field, and varying an electrical stimulus applied to at least first and second shielding electrodes of the plurality of electrodes to vary a distribution of the electric field in three spatial dimensions.

20. The apparatus of claim 1, wherein the lead has a substantially circular cross-section in a plane substantially orthogonal to the longitudinal axis, and wherein the substantially constant width comprises a substantially constant diameter.

21. The method of claim 8, wherein the lead has a substantially circular cross-section in a plane substantially orthogonal to the longitudinal axis, and wherein the substantially constant width comprises a substantially constant diameter.

22. The apparatus of claim 13, further comprising a stimulation generator configured to generate electrical stimulation delivered via the electrodes and a controller configured to control steering of a stimulation field generated by the delivery of the electrical stimulation.

23. The apparatus of claim 22, further comprising an implantable medical device configured to be coupled to the lead, wherein the implantable medical device includes at least one of the stimulation generator or the controller.

24. The apparatus of claim 22, wherein the controller is configured to control the steering of the stimulation field by at least applying an electrical stimulus via a first stimulating electrode of the plurality of electrodes to generate a stimulating electric field, and varying an electrical stimulus applied to at least first and second shielding electrodes of the plurality of electrodes to vary a distribution of the stimulating electric field in three spatial dimensions.

25. The apparatus of claim 13, wherein the lead has a substantially circular cross-section in a plane substantially orthogonal to the longitudinal axis, and wherein the substantially constant width comprises a substantially constant diameter.

26. The apparatus of claim 1, wherein the field is steerable in a temporal dimension.

27. The apparatus of claim 1, wherein the two-dimensional array includes a regular array.

28. The apparatus of claim 5, wherein the fiducial marker includes a rotationally asymmetric portion adapted to engage a stereotactic head frame.

29. The apparatus of claim 1, further comprising means for electrically stimulating the electrodes according to a spatially and temporally varying electrical stimulation scheme.

30. The apparatus of claim 29, wherein the stimulation scheme is longitudinally asymmetric.

31. The apparatus of claim 1, further comprising means for selectively exciting the electrodes according to a unipolar and a bipolar electrical stimulation pattern.

32. The apparatus of claim 1, further comprising a flexible circuit substrate and wherein at least one of said electrodes is carried by the substrate.

33. The apparatus of claim 1 further comprising a flexible monolithic electrical circuit carried by the lead and in operative electrical communication with at least one of said electrodes.

34. The apparatus of claim 1, wherein the array includes first and second longitudinally displaced columns, the first and second columns include a longitudinal pitch, and the first and second columns are offset by a distance which is less than the pitch.

35. The method of claim 8, wherein the lead includes a hexagonally-shaped electrode.

36. The method of claim 35, wherein the electrodes are disposed in a close-packed two dimensional array.

37. The method of claim 8, wherein the electrodes are disposed in a two dimensional array including at least first and second adjacent, longitudinally displaced rows, the first and second rows include an angular spacing, and the first and second rows are angularly offset by a non-zero fraction of the angular array spacing.

38. The method of claim 8, further comprising varying the electrical stimulus applied to at least one of the first and second shielding electrodes to vary a temporal distribution of the electric field.

39. The method of claim 8, further comprising varying an electrical stimulus applied to the plurality of electrodes to generate an electric field which rotates about the longitudinal axis, wherein the electric field exhibits rotational symmetry.

40. The method of claim 8, further comprising determining a rotational orientation of the lead in relation to the tissue and using the determined orientation to select the first stimulating electrode.

41. The apparatus of claim 13, wherein the electrodes are each hexagonal in shape.

42. The apparatus of claim 13, wherein the array includes first and second longitudinally displaced columns, the first and second columns include a longitudinal pitch, and the first and second columns are offset by a distance which is less than the pitch.

* * * * *